United States Patent [19]

Hoekwater et al.

[11] Patent Number: 4,919,389
[45] Date of Patent: Apr. 24, 1990

[54] LARGE BORE TUBING ROLLER CLAMP

[75] Inventors: Mark A. Hoekwater, Mundelein; Anthony R. Paren, Hawthorn Woods; Thomas Kasting, McHenry; Richard Rollins, Mundelein, all of Ill.

[73] Assignee: Baxter International Inc., Deerfield, Ill.

[21] Appl. No.: 324,850
[22] Filed: Mar. 17, 1989
[51] Int. Cl.⁵ .................................................. F16K 7/06
[52] U.S. Cl. ........................................... 251/6; 251/4
[58] Field of Search ........................................ 251/4, 6

[56] References Cited

U.S. PATENT DOCUMENTS 4,238,108 12/1980 Muetterties ........................... 251/6
4,725,037 2/1988 Adellery ................................. 251/6

Primary Examiner—John Fox
Attorney, Agent, or Firm—Paul C. Flattery; Amy L. H. Rockwell

[57] ABSTRACT

A large bore tubing roller clamp assembly for regulating the flow rate of a liquid through large bore tubing is disclosed. The roller clamp assembly comprises a substantially rigid elongated plastic frame, a generally cylindrical roller, and a length of a large bore tubing disposed within the frame. The flow rate through the tubing is controlled by moving the roller along an inclined roller track and over the tubing, thereby selectively compressing tubing to attain the desired flow rate.

6 Claims, 3 Drawing Sheets

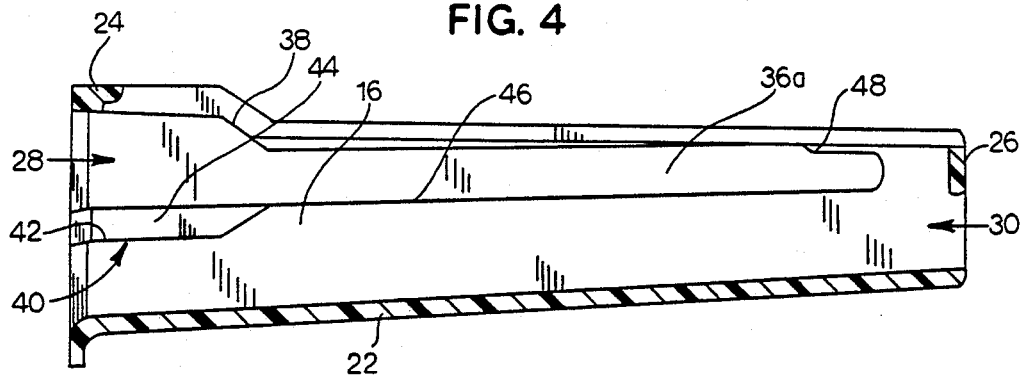
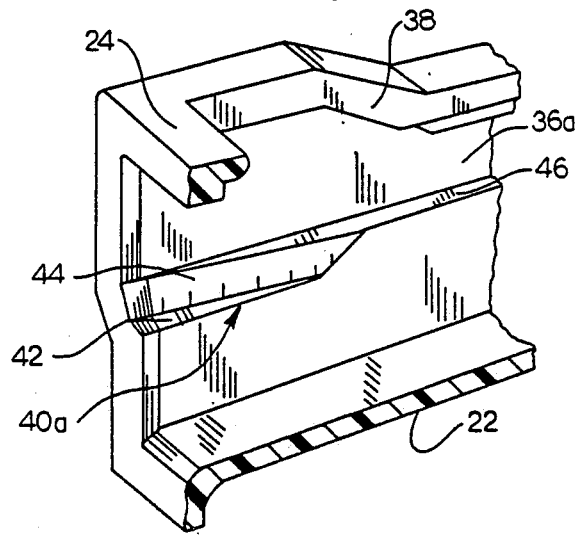
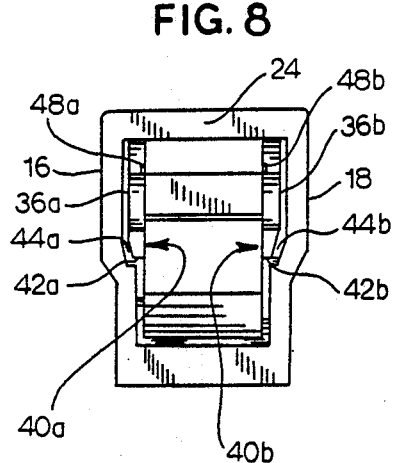
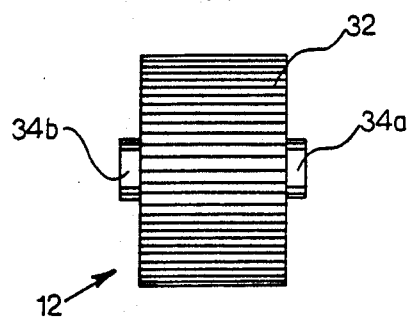
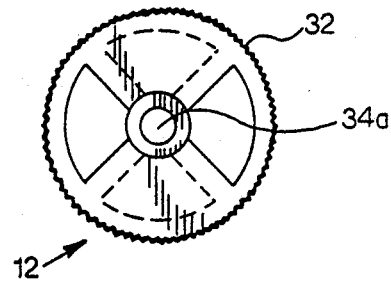

LARGE BORE TUBING ROLLER CLAMP

BACKGROUND OF THE INVENTION

The present invention relates generally to roller clamps for regulating the flow rate of a liquid through large bore plastic tubing.

Roller clamps are well-known devices for controlling the flow of liquid through plastic tubing, such as used in intravenous administration sets and other medical applications. Roller clamps have heretofore generally included an elongated frame, a movable roller disposed within the frame, and tubing extending through the frame. The flow of liquid through the tubing is regulated by moving the roller along an inclined path over the tubing within the frame. Movement of the roller selectively compresses or releases the tubing, thereby varying the flow path so as to attain a selected flow rate.

The use of roller clamps to regulate the flow of liquid through tubing is well known and has been particularly useful in controlling the flow of medical or medically-related liquids during surgical or post-operative procedures. Manufacturers of these clamps include Baxter Healthcare Corporation of Deerfield, Ill., and numerous others. Although roller clamps previously manufactured have generally worked satisfactorily, they suffer from certain drawbacks when applied to flow control in large bore plastic tubing, where high flow rates are necessary.

Large bore tubing, as used here, means tubing having an inside diameter of at least about 0.19 inches (4.83 mm) and a wall thickness of at least about 0.04 inches (1.02 mm). For example, in a transuretheralresectomy (TUR), a flow rate of up to 1000 ml/hr of sterile water is required as part of the procedure, thus requiring large bore tubing for directing the flow of water from the source container to the procedure site or instrument.

Roller clamps of existing design have displayed a number of deficiencies in such applications. One such difficulty is in accurate and/or lack of sustained fluid flow rate control including the inability to maintain a complete shut-off position over a lengthy period of time, e.g., twenty-four hours. Another problem often encountered is roller clamp breakage or roller "pop-out," which occurs when the roller comes out of the frame or disengages from roller tracks in which it moves.

These difficulties are believed to be particularly acute in large bore tubing applications because of high stress imposed on the roller clamp in such applications. In the full shut-off position, in particular, the stress imposed on roller clamp assembly is especially high, and undue flexibility in the roller clamp frame is believed to have resulted in one or more of the above-described drawbacks.

Accordingly, it is a general object of the present invention to provide a large bore tubing roller clamp assembly which does not suffer from the drawbacks described above.

It is a more specific object of the present invention to provide a large bore tubing roller clamp assembly which can withstand the stress imposed while providing reliable flow control rates, including complete and sustained shutoff capability.

SUMMARY OF THE INVENTION

The present invention is directed to a large bore tubing roller clamp assembly for regulating the flow rate of a liquid through large bore tubing. More specifically, the present invention is directed to a roller clamp assembly which comprises a substantially rigid, elongated plastic frame, a cylindrical roller, and a length of a large bore tubing. Large bore tubing, as used here, means tubing having an inner diameter of at least about 0.19 inches (4.83 mm) and a wall thickness of at least about 0.04 inches (1.02 mm).

In the preferred embodiment, the roller clamp frame includes a pair of side walls, a flat bottom wall and a top wall portion. The top wall portion defines an elongated aperture through which a part of the roller protrudes for manual manipulation. A bridge member joins the side walls at each end of the frame and defines end apertures through which the large bore tubing extends. At least one of these end apertures is also large enough to allow for initial insertion or mounting of the roller into the frame.

The roller is generally cylindrical in shape and has axles located at the center of each face of the roller. Insertion of the roller is facilitated by a loading ramp comprising pathways located along the inner surfaces of each of the side walls for receiving the axles of the roller. This loading ramp originates at the roller receiving end aperture and merges into a roller track which extends along the inside surface of each side wall of the frame. Once situated within the roller track, a portion of the roller protrudes through the aperture in the top wall portion, allowing for manual movement of the roller along the frame.

The large bore tubing is situated between the flat bottom of the frame and the movable roller and extends through each of the end apertures. Fluid flow is regulated by moving the roller over the length of tubing. The roller track extends at an incline relative to the flat bottom wall, and movement of the roller down the incline selectively compresses the tubing, changing the relative opening therethrough and, as a result, controlling the flow of fluid. A fully open position is achieved when the roller is at the end of the roller track spaced farthest from the flat bottom and is not exerting any pressure on the tubing. A fully closed position is reached when the roller is at the other end of its travel along the roller track and located in the position closest to the bottom wall, where no fluid flows through the tubing. Intermediate positions between the fully closed and fully opened positions may be achieved by moving the roller to a position yielding the desired flow rate. In the present invention, once the roller has been set to attain the flow rate desired, the flow rate will remain substantially constant, including a zero flow rate in the fully closed position, for an extended period of time.

In the present invention, the fully closed position is achieved at a roller position which is spaced from the end of the frame and from the most distal end point of the roller track. To prevent undue stress from being imposed on the roller clamp, movement of the roller past the fully closed position is inhibited by a shoulder in the roller track which restricts movement of the roller axles beyond this position.

The rigid structure of the roller clamp assembly of the present invention also enhances the ability of the entire assembly to withstand the increased stresses associated with flow control in large bore tubing. This added rigidity is due, at least in part, to the bridge members located at each end of the frame. As a result, in the preferred embodiment the roller can remain in the fully closed position for up to forty-eight hours during use of the roller clamp assembly without substantial leakage or roller displacement.

Further features of the present invention will become more fully apparent in the following detailed description of the drawings and in the appended claims.

DESCRIPTION OF THE DRAWINGS

FIG. 2 is an elevational view of the roller employed in the clamp assembly of FIG. 1.

FIG. 3 is a side view of the roller of FIG. 2.

FIG. 4 is a cross-sectional side view of the frame only employed in the roller clamp assembly of FIG. 1.

FIG. 7 is an enlarged fragmentary perspective view of the frame of the roller clamp assembly of FIG. 1, depicting the roller loading ramp.

FIG. 8 is an end view of the roller clamp frame, taken from the roller-receiving end.

DETAILED DESCRIPTION OF THE INVENTION

Figure 1:
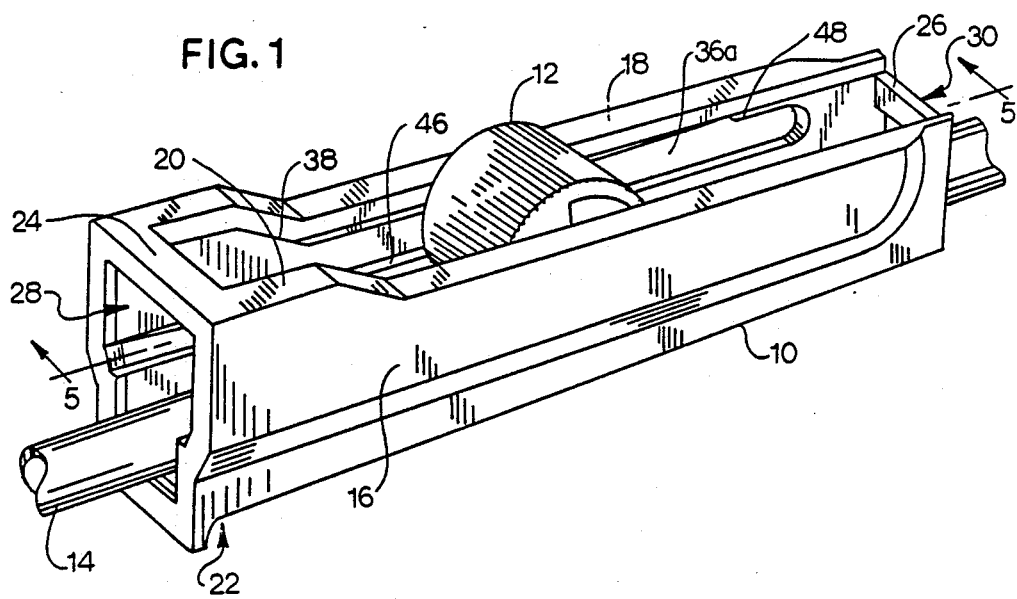
FIG. 1 is a perspective view of the roller clamp assembly of the present invention.

As shown in FIG. 1, the present invention is generally embodied in a roller clamp assembly comprising a frame 10, a roller 12 disposed within the frame, and a length of large bore tubing 14 extending through the frame.

The frame itself is preferably injection molded as one integral piece of rigid plastic material. The frame is generally elongated with a pair of side walls 16 and 18, a substantially open top wall portion 20 and a flat bottom wall 22. Bridge members 24 and 26 at each end of the frame join side walls 16 and 18 and define an elongated aperture or opening within top wall portion 20, through which a portion of the roller protrudes.

Figure 9:
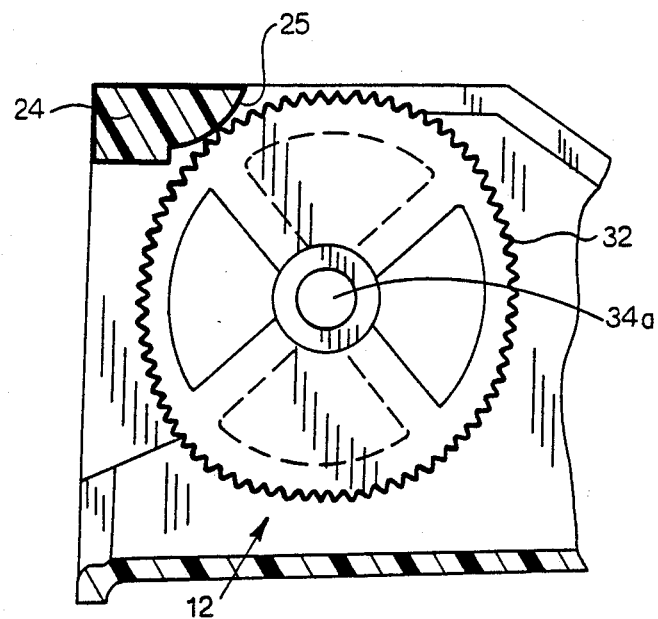
FIG. 9 is an enlarged, sectional view of the roller in contact with a bridge member at the roller receiving end of the frame.

Each end of the frame 10 also is open. More specifically, side walls 16 and 18, bottom wall 22 and bridge member 24 define a relatively large aperture 28 at one end of the frame through which the roller 12 is loaded into the frame, and through which the large bore tubing 14 extends. As shown in FIG. 9, the inner surface 25 of bridge member 24 is smooth and convex to prevent the roller from sticking or adhering to the bridge member 24 when the roller comes into contact with the bridge member. The interior surfaces of side walls 16 and 18 and bottom wall 22 are preferably chamfered at the large aperture end to enhance roller operation generally. A smaller aperture 30, through which the tubing also extends, is defined at the other end of the frame by the side walls 16 and 18, bottom wall 22 and bridge member 26.

FIGS. 2 and 3 show the roller 12 employed in the present invention. The roller is generally cylindrical, with a serrated or ribbed surface 32 to enhance frictional contact for digital manipulation by the user's thumb or finger. For mounting and movement of roller 12 within frame 10, cylindrical axles 34a and 34b extend from the center of each side of the roller. Although the roller may be constructed from a variety of materials, it is preferably injection molded from rigid plastic material.

Figure 5:
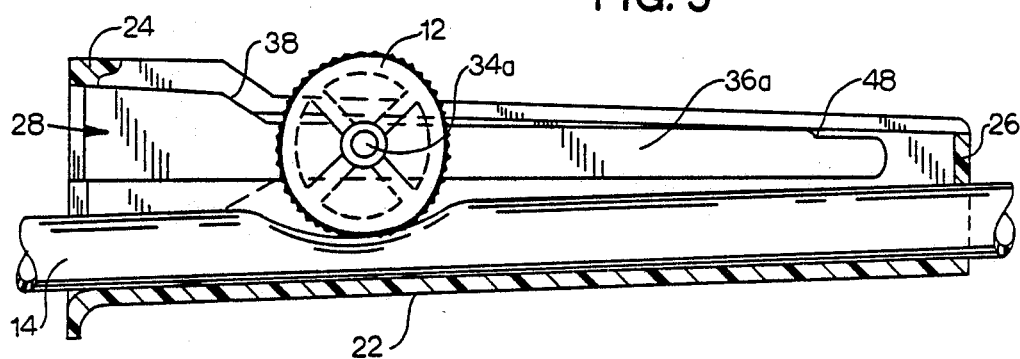
FIG. 5 is a cross-sectional side view, taken along line 5—5 of FIG. 1, with the roller in an intermediate position between the left-most fully open position and right-most fully closed position.
Figure 6:
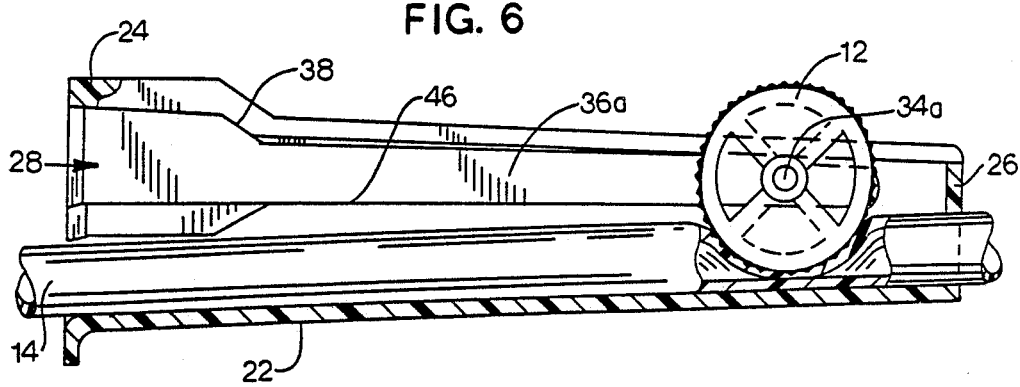
FIG. 6 is a cross-sectional side view of the roller clamp assembly of FIG. 1, with the roller in the fully closed position.

The roller 12, during normal use, is located within the frame 10, as best seen in FIGS. 1, 5 and 6. Specifically, axles 34a and 34b are situated within roller tracks 36a and 36b located along the inside surface of each of the side walls 16 and 18 as shown in FIGS. 5 and 6. Each roller track 36 is a generally recessed groove which extends substantially along the length of frame 10 and at an angle in relation to the flat bottom wall 22, as seen in FIG. 4. Thus, movement of the roller 12 along the roller track 36 selectively increases or decreases the distance between the flat bottom wall 22 and the roller surface 32. As noted above, when inserted into the tracks, a portion of the roller 12 protrudes through the opening in top wall portion 20 (as shown in FIG. 1) to allow for manual movement of the roller 12 along the length of the frame.

The present invention, as described in the summary, is directed to a roller clamp assembly for controlling flow in large bore plastic tubing. For purposes of this description, "large bore tubing" is tubing which can provide relatively large flow rates, such as required, for example, in transuretheralresectomy ("TUR"), where a flow rate of up to or exceeding 1000 ml/hr of sterile water may be required as part of the procedure. In the preferred embodiment, the large bore tubing of the present invention has an inner diameter of not less than 0.19 inches (4.83 mm). Although the tubing may vary in thickness, it is preferred that the tubing used with the present invention have a wall thickness of not less than 0.04 inches (1.02 mm). As shown in FIG. 1, the large bore tubing 14 extends through the end apertures 28 and 30 of the frame 12, with the portion of tubing within the frame 10 situated between the roller 12 and the flat bottom 22.

Fluid flow through the tubing 14 is regulated by moving the roller 12 over the length of tubing 14. Because the roller track 36a and 36b is at an angle relative to the flat bottom 22 (as described above), movement of the roller 12 along the track 36a and 36b selectively compresses or relieves the tubing, changing the size of the inner flow path through the tubing and, as a result, controlling the flow of fluid.

Thus, as shown in FIG. 5, when the roller 12 is located near end aperture 28, it exerts little pressure on the tubing 14, leaving the fluid flow path substantially open. Movement of the roller in the direction of end aperture 28 further relieves the pressure on the tubing. In fact, placement of the roller between end aperture 28 and shoulder 38 (commonly designated as the "fully open" position) results in no significant compression of the tubing and allows the flow of fluid through the tubing to remain completely uninhibited. FIG. 6 shows the roller moved nearer the other end aperture 30 of the frame 10 and in what is commonly known as the fully closed position. This means that when the roller 12 is moved to this position, it fully and completely compresses the tubing 14 to yield a flow rate of zero. Naturally, intermediate flow rates can be attained by moving the roller to an intermediate position along the roller track to yield the desired flow rate.

For ease of insertion of roller 12 into frame 10, loading ramps 40a and 40b are located along the inner surface of each of the side walls, as best seen in FIG. 7. Generally, each ramp 40a and 40b begins at the roller receiving end aperture 28, and curves upwardly to merge with the roller track 36a or 36b, respectively. More specifically, each loading ramp has a flat ledge portion 42 and a loading ramp wall portion 44 which extends between the ledge 42 and the respective roller track 36a or 36b. Each of the loading ramp wall portions 44 begins at the roller receiving end aperture 28 and angles inwardly and upwardly to direct the roller axles into the roller tracks 36. The frame 12, while essentially rigid, has a slight resilience which allows temporary flexing for installation of the roller into the tracks. Once the axles 34a and 34b are situated within the recessed grooves of the roller track, roller track ledge 46, which extends substantially completely to the end aperture 28, prevents the roller from slipping off the track 36.

The present invention is particularly well-suited for use in medical procedures requiring rapid flow rates and utilizing large bore tubing. As discussed earlier, regulating flow rates through large bore tubing generally places a great deal of strain or stress on both the roller and the frame. In existing roller clamps, the flexibility of the material and structural design often lead to roller displacement and consequently unreliable flow rates.

In accordance with the present invention, however, a roller clamp is provided which is capable of withstanding the increased stress associated with flow rate control in large bore tubing. In the preferred embodiment of the present invention, for example, obstruction means in the form of a shoulder 48a and 48b is provided along the roller track 36 spaced from aperture end 30 to inhibit movement of the roller beyond the shoulder, as shown in FIG. 4. Thus, the fully closed position can be attained without moving the roller all the way to the end of the frame, thereby preventing undue strain from being applied when the roller goes to the very end of the roller track. This allows the increased stress which normally results from completely shutting off the flow of fluid through large bore tubing to be distributed more evenly over the body of the frame. Bridge members 24 and 26 also provide rigidity to the frame and decrease the chance that the frame will flex and allow the roller 12 to become displaced from its selected position along the roller track 36.

These and other features of the present invention have been depicted in the attached drawings for illustrative purposes only, and it is not intended that the present invention be limited to the precise embodiment shown here.

What is claimed is:

1. A large bore tubing roller clamp assembly for regulating the flow rate of a liquid through large bore tubing, said assembly comprising a substantially rigid elongated plastic frame, a generally cylindrical roller, and a length of a large bore tubing disposed within said frame, said frame having:
    a pair of side walls, a flat bottom wall, and a top wall portion defining an elongated aperture therein, said aperture being defined, in part, by a first bridge member joining said side walls at one end of said frame, and a second bridge member joining said side walls at the opposite end of said frame;
    said frame further comprising means defining apertures at each end of said frame for receiving large bore tubing therethrough, wherein the aperture at one end further serves as a roller receiving aperture for receiving said roller therethrough;
    said frame further having a roller track comprising a recessed pathway located along the inner surface of each of said side walls beginning from said end defined by said roller receiving aperture and extending substantially along the length of said frame, said roller track being disposed at an incline relative to said flat bottom wall;
    said frame still further comprising a loading ramp for loading said roller into said roller track, said loading ramp being defined along the inner surfaces of each of said side walls and below said recessed pathways of said roller track, said loading ramp beginning from the end defined by said roller receiving aperture and extending upwardly to merge with said roller track to facilitate insertion of said roller into said frame;
    said roller being disposed within said frame and being rollingly movable along said frame,
    said roller having means defining an axle at the center of each face of said roller, said axle means being disposed within the recessed pathways of said roller tracks to permit movement of said roller along of said frame;
    a portion of said roller protruding through said aperture of said top wall portion for manual movement of said roller;
    said large bore tubing being disposed within said frame between said roller and said flat bottom wall and extending through each of said end apertures, whereby the flow-rate of a liquid therethrough is controlled by moving said roller over said tubing between a fully open position at one end of said roller track and a fully closed position spaced from the other end of said roller track, the flow rate through said tubing being substantially uninhibited when the roller is disposed in said fully open position, said flow rate decreasing as said roller is moved from said one end and gradually compresses tubing, thereby decreasing the fluid pathway through the interior of said tubing, said flow rate being defined by a flow-rate of zero when said roller is in said fully closed position; and
    said frame further comprising obstruction means disposed along said roller track at said fully closed position to inhibit movement of said roller beyond said fully closed position, said obstruction means being spaced from the other end of said roller track.

2. A large bore tubing roller clamp assembly in accordance with claim wherein said obstruction means comprises a shoulder defined in said roller track.

3. A large bore tubing roller clamp assembly as described in claim 1 wherein said large bore tubing has an inner diameter of not less than about 0.19 inches and a wall thickness of not less than about 0.04 inches.

4. A large bore tubing roller clamp assembly as described in claim 3 wherein said roller clamp is capable of controlling flow rates from 0–1000 ml/hour at a substantially constant rate and for twenty-four hours without displacement or movement of said roller.

5. A large bore tubing roller clamp assembly as described in claim 3 wherein during use of said assembly, said fully closed position is free of leakage through said tubing for a period of up to forty-eight hours.

6. A large bore tubing roller clamp assembly as described in claim 1 wherein said first bridge member is adjacent to the roller receiving aperture and said first bridge member includes surface means for non-adhering contact with said roller.

* * * * *

UNITED STATES PATENT AND TRADEMARK OFFICE
CERTIFICATE OF CORRECTION

PATENT NO. :   4,919,389

DATED      :   April 24, 1990

INVENTOR(S) :  Mark A. Hoekwater et al.

It is certified that error appears in the above-identified patent and that said Letters Patent is hereby corrected as shown below:

Col. 6, line 48;   Claim 2, after "in accordance with claim" insert --1--

Signed and Sealed this

Twenty-eighth Day of April, 1992

Attest:

HARRY F. MANBECK, JR.

*Attesting Officer*        Commissioner of Patents and Trademarks